United States Patent [19]
Coffee

[11] Patent Number: 6,105,571
[45] Date of Patent: *Aug. 22, 2000

[54] DISPENSING DEVICE

[75] Inventor: Ronald Alan Coffee, Haslemere, United Kingdom

[73] Assignee: Electrosols, Ltd., Surrey, United Kingdom

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/492,204

[22] Filed: Jun. 2, 1995

Related U.S. Application Data

[63] Continuation of application No. PCT/GB93/02634, Dec. 22, 1993.

[30] Foreign Application Priority Data

Dec. 22, 1992 [GB] United Kingdom .................. 9226717

[51] Int. Cl.[7] .......................... A61M 11/00; A61M 15/00; B05B 5/00
[52] U.S. Cl. ................................ 128/200.14; 128/200.23; 128/203.12; 239/690
[58] Field of Search .................. 138/200.14, 200.23, 138/200.16, 203.12; 239/102.2, 690, 690.1, 697, 706

[56] References Cited

U.S. PATENT DOCUMENTS

| | | |
|---|---|---|
| 2,723,646 | 11/1955 | Ransburg . |
| 2,945,443 | 7/1960 | Aver et al. . |
| 3,096,762 | 7/1963 | Winchell ................................ 128/190 |
| 3,131,131 | 4/1964 | Wehner . |
| 3,232,292 | 2/1966 | Schaefer ................................. 128/172 |
| 3,456,646 | 7/1969 | Phillips et al. ..................... 128/200.23 |

(List continued on next page.)

FOREIGN PATENT DOCUMENTS

| | | |
|---|---|---|
| 0 029 301 | 12/1984 | European Pat. Off. . |
| 0 102 713 B1 | 9/1987 | European Pat. Off. . |
| 0 234 842 | 9/1987 | European Pat. Off. . |
| 0250164A3 | 12/1987 | European Pat. Off. . |
| 0523963A1 | 7/1992 | European Pat. Off. . |
| 0523962A1 | 1/1993 | European Pat. Off. . |
| 523964A1 | 1/1993 | European Pat. Off. . |
| WO 93/06937 | 4/1993 | European Pat. Off. . |
| 2008769 | 9/1970 | Germany . |
| 4106564A1 | 9/1992 | Germany . |
| 195704 | 12/1980 | New Zealand . |
| 198774 | 10/1981 | New Zealand . |
| 191545 | 6/1984 | New Zealand . |
| 1005939 | 6/1981 | U.S.S.R. . |
| 1297993 | 11/1972 | United Kingdom . |
| 2018627 | 10/1979 | United Kingdom . |
| 1 569 707 | 6/1980 | United Kingdom . |
| 2 018 627 | 4/1982 | United Kingdom . |
| 2 128 900 | 5/1984 | United Kingdom . |
| 2 201 873 | 9/1988 | United Kingdom . |
| WO 91/07232 | 5/1991 | WIPO . |
| WO 92/15339 | 9/1992 | WIPO . |

OTHER PUBLICATIONS

Article entitled: Electro–osmosis Controls Fluid in Novel Transducer Concept by Product Engineering, dated Jul. 4, 1970 authored by: Ray Lewis, Cleveland; pp. 71–72.

Article entitled: Electrodynamic Crop Spraying, dated 1981; authored by: R. A. Coffee; Reprinted from Outlook on Agriculture vol. 10, No. 7, 1981; includes excerpt pp. 350–356.

Article entitled: Charging Liquid Spray by Electrostatic Induction authored by: S. E. Law and H. D. Bowen; taken from Transactions of the ASAE; pp. 501–506; dated 1966.

*Primary Examiner*—John G. Weiss
*Assistant Examiner*—Todd Martin
*Attorney, Agent, or Firm*—Cobrin & Gittes

[57] ABSTRACT

An electrohydrodynamic dispensing device for comminuting a liquid which comprises a comminution site, a means for supplying liquid to the comminution site and a means for inducing an electrical charge at the comminution site sufficient to comminute the liquid supplied to it.

26 Claims, 4 Drawing Sheets

U.S. PATENT DOCUMENTS

| | | | |
|---|---|---|---|
| 3,837,573 | 9/1974 | Wagner | 239/705 |
| 3,897,905 | 8/1975 | Tadewald | 239/706 |
| 3,930,061 | 12/1975 | Schaefenberger | 427/27 |
| 3,958,959 | 5/1976 | Cohen et al. | 55/10 |
| 4,043,331 | 8/1977 | Martin et al. . | |
| 4,044,404 | 8/1977 | Martin et al. . | |
| 4,073,002 | 2/1978 | Sickles et al. | 239/690.1 |
| 4,150,644 | 4/1979 | Masaki et al. | 123/119 |
| 4,186,886 | 2/1980 | Sickles | 239/690.1 |
| 4,198,781 | 4/1980 | Dykes . | |
| 4,203,398 | 5/1980 | Maruoka | 123/119 |
| 4,266,721 | 5/1981 | Sickles | 239/3 |
| 4,356,528 | 10/1982 | Coffee | 361/226 |
| 4,380,786 | 4/1983 | Kelly . | |
| 4,439,980 | 4/1984 | Biblarz et al. | 60/39.06 |
| 4,467,961 | 8/1984 | Coffee et al. | 239/1 |
| 4,476,515 | 10/1984 | Coffee | 239/690 |
| 4,508,265 | 4/1985 | Jido | 239/3 |
| 4,509,694 | 4/1985 | Inculet et al. | 239/697 |
| 4,549,243 | 10/1985 | Owen et al. | 361/228 |
| 4,659,012 | 4/1987 | Coffee | 239/3 |
| 4,671,269 | 6/1987 | Wilp | 128/202.25 |
| 4,703,891 | 11/1987 | Jackson et al. . | |
| 4,735,364 | 4/1988 | Marchant | 239/690.1 |
| 4,748,043 | 5/1988 | Seaver et al. | 427/30 |
| 4,749,125 | 6/1988 | Escallon et al. | 239/3 |
| 4,776,515 | 10/1988 | Michalchik | 239/706 |
| 4,788,016 | 11/1988 | Colclough et al. | 264/10 |
| 4,801,086 | 1/1989 | Noakes | 239/3 |
| 4,830,872 | 5/1989 | Grenfell . | |
| 4,846,407 | 7/1989 | Coffee | 239/690 |
| 4,962,885 | 10/1990 | Coffee | 239/3 |
| 4,979,680 | 12/1990 | Bauch et al. | 239/692 |
| 5,044,564 | 9/1991 | Sickles | 239/690.1 |
| 5,086,972 | 2/1992 | Chang et al. | 239/3 |
| 5,115,971 | 5/1992 | Greenspan et al. . | |
| 5,180,288 | 1/1993 | Richter et al. . | |
| 5,222,663 | 6/1993 | Noakes et al. | 239/691 |
| 5,267,555 | 12/1993 | Pajalich | 128/200.14 |
| 5,381,789 | 1/1995 | Marquardt | 128/202.25 |
| 5,402,945 | 4/1995 | Swanson . | |
| 5,409,162 | 4/1995 | Sickles | 239/690.1 |
| 5,483,953 | 1/1996 | Cooper | 128/200.14 |
| 5,655,517 | 8/1997 | Coffee . | |

DISPENSING DEVICE

This is a continuation PCT application Ser. No. PCT/GB93/02634 filed Dec. 22, 1993, now pending, which is a continuation of GB 9226717.8 filed on Dec. 22, 1992.

SCOPE OF THE INVENTION

The invention relates to a dispensing device for comminuting a liquid and the uses of such a device, especially in medicine.

BACKGROUND

Dispensing devices are known which produce a finely divided spray of liquid droplets by electrostatic (more properly referred to as 'electrohydrodynamic') means. The droplet spray in such devices is generated by the application of an electric field to a liquid at a spray head or spray edge. The potential of the applied electric field is sufficiently high to provide comminution of the liquid from the spray head. The droplets produced are electrically charged and thus are prevented from coagulating by mutual repulsion.

Electrohydrodynamic sprayers have potential uses in many areas, including agriculture and the automotive industry and also for dispensing cosmetics and medicines.

United Kingdom patent number 1569707 describes such an electrohydrodynamic spray device principally for use in crop spraying.

United Kingdom patent number 2018627B discloses an electrohydrodynamic spray device wherein the charged droplet spray is fully or partially electrically discharged by means of an earthed electrode having a sharp or pointed edge and located downstream of the spray head. European Patent number 0234842 also uses this technology and relates to an inhaler in which charged droplet spray is discharged prior to inhalation by means of a sharp or pointed discharge electrode carrying an opposite charge to the droplet spray and located downstream of the spray head. The droplets are discharged to facilitate droplet deposition into the respiratory tract by preventing deposition of charged droplets onto the mouth and throat of the user.

A common feature of all known electrohydrodynamic spray devices is that the electric charge used to generate the spray is applied directly to the spray head. It has now surprisingly been found that the direct application of the field is not essential and that the electrohydrodynamic comminution of a liquid may be accomplished by inducing the required electric charge at the spray head. In addition and advantageously, it has been found that the comminutions produced can be partially or fully discharged prior to use.

This method of induced charging has been found to provide better comminution of liquids having lower electrical resistivity.

SUMMARY OF THE INVENTION

Accordingly, it is one aspect of the invention that there is provided an electrohydrodynamic dispensing device for comminuting a liquid, wherein the liquid is comminuted by an induced electrical charge.

In yet a further aspect, the means for fully or partially discharging the liquid comminution is provided by an electrode arranged to have a first surface capable of producing an electric field sufficient to induce the required charge for liquid comminution in the comminution means and also to impart sufficient inertia to the liquid comminution so that it substantially bypasses the first surface, the electrode also having a second surface capable of producing an ionic discharge to fully or partially discharge the liquid comminution.

The dispensing device normally comprises a comminution site, a means for supplying liquid to the comminution site and a means for inducing an electrical charge at the comminution site sufficient to comminute the liquid.

The comminution site may be any conventional electrohydrodynamic comminution site such as a surface or edge generally provided by a thin capillary tube, a nozzle or a slot defined by two parallel plates.

Appropriate means for supplying liquid to the comminution site include mechanical or electrically powered pumps which are capable of providing the required flow rate of liquid to the comminution site such as a syringe pump or the electrically powered pump described in EP 0029301.

The comminution means of the invention can be used with a large range of flow rates, but generally operates with flow rates in the range of between 0.1 to 500 $\mu$L per second, such as 0.5 to 5 $\mu$L per second, especially for inhaled administration, or 10 to 200 $\mu$L per second, especially for agricultural use.

The means for inducing the electrical charge at the comminution site may be any conventional source of electrical charge which in use is capable of inducing a charge sufficient to comminute the liquid from the comminution means including a high voltage generator or a piezoelectric generator. The charge required is usually of the order of 1–20 kilovolts for example 10 kilovolts.

After formation of the liquid comminution, the electrically charged liquid droplets are attracted towards and will impact the means for inducing the electrical charge at the comminution site. In a preferred aspect of the present device, there is therefore provided a means for partially or fully electrically neutralizing the liquid comminution before it impacts the induced charging means.

One suitable means for partially or fully electrically discharging the liquid comminution is a sharp or pointed discharge electrode located downstream of the comminuted liquid.

The sharp or pointed discharge electrode may be earthed or it may be maintained at a polarity opposite to that of the induced charging means by connection to a suitable charging means. In either case the comminuted liquid is partially or fully discharged by a cloud of charged ions produced from the surrounding air having an opposite electrical charge to that on the comminuted liquid spray. The ion cloud is attracted towards, collides with and thereby partially or fully discharges the liquid spray.

In one particularly advantageous form of the device, the means for fully or partially discharging the liquid comminution is provided by a combination of the sharp or pointed discharge electrode and at least one capacitor, the capacitor acting to absorb the charge from the gaseous ions from the sharp or pointed discharge electrode until the induced comminution of the liquid is established, the capacitor is arranged to absorb the ions until it reaches a predetermined potential at which potential it ceases to absorb the ions thereby allowing them to partially or fully discharges the liquid comminution.

Generally, the capacitor is chosen to have a time constant having the same order as the time required to establish the liquid comminution spray cloud. Thus the time constant will have a value, in seconds, which is the product of the capacitance, C and the resistance, R, of the capacitor.

The value of CxR for the capacitor is chosen so that the capacitor will charge until it reaches a prearranged potential sufficient to modify the electric field, the capacitor then discharges towards the established spray cloud. Generally, the time-constant required will be of the order of seconds or a number of milliseconds. For example, a capacitor of 0.1 microfarad with a resistance of 10 megohms will produce a time constant of one second.

In yet a further aspect, the means for fully or partially discharging the liquid comminution is provided by an electrode arranged to have a first surface capable of producing an electric field sufficient to induce the required charge for liquid comminution in the comminution means and also to impart sufficient inertia to the liquid comminution so that it substantially bypasses the first surface, the electrode also having a second surface capable of producing an ionic discharge to fully or partially discharge the liquid comminution.

Generally, the second surface is shaped to have a sharp edge or a point which in use produces the ionic discharge.

Suitably, the electrode is an annular electrode coaxially located with respect to the intended flight path of the liquid comminution, in use the upper surface of the annular electrode induces the required charge in the comminution means, the lower surface being shaped so as to produce the ionic discharge.

In operation the field pattern of the upper surface of the annular electrode is such that the comminution is directed onto an axial flight path with respect to the annular electrode and is provided with sufficient inertial force to substantially bypass the first surface, the comminution is then fully or partially discharged by the gaseous ions produced by the second surface.

The device of the invention may be used to dispense liquids comprising components useful for human or animal health care, such as medicaments for pharmaceutical or public health care use or medically useful compounds such as anesthetics.

Suitable liquids include liquids comprising components for agricultural use such as pesticides or biocides.

Suitable liquids include liquid cosmetic formulations.

Other suitable liquids include paints and inks. Also included are liquids for providing aromas.

Preferred liquids are pharmaceutically active liquids.

The comminution means of the dispenser provides liquid droplets within the range of from about 0.1 to about 500 microns in diameter: More usually from 0.1 to 200 microns, such is 1.0 to 200 microns: Examples include droplets within the range of 5.0 to 100, 0.1 to 25, 0.5 to 10 or 10 to 20 microns. A favoured range for inhaled administration is 0.1 to 25 or 0.5 to 10 microns, especially for administration to the lower respiratory tract, and 10 to 25 microns, especially for administration to the upper respiratory tract.

For a given liquid the diameter of the droplets can be controlled by varying the applied voltage and liquid flow rate using routine experimental procedures. Liquids having viscosities within the range of from 1 to 500 centipoise and resistivities in the range of from $10^2$–$10^8$ ohm m can be comminuted by the present device.

As stated this method of induced charging has been found to provide better comminution of liquid having a lower electrical resistivity, such as is the case of aqueous solvents, including solvent mixtures, and solutions thereof and low resistivity organic solvents such as alcohols.

One favoured use of the device of the invention is for the dispensation of a comminuted liquid for inhalation.

Accordingly, in one preferred aspect of the invention there is provided a device for comminuting a liquid for inhalation, wherein the liquid is comminuted by an induced electrical charge.

The device of the invention may be adapted into any embodiment form which dispenses comminuted liquid for inhalation, for both medicinal and non-medicinal use.

Non-medicinal inhalation uses includes dispensing perfumes and aromas.

Preferably, the device is in the form of an inhaler, for the inhaled delivery of a medicament.

A preferred liquid is therefore a liquid medicament formulation adapted for inhaled administration.

Medicaments suitable for adaption for inhaled administration include those used for the treatment of disorders of the respiratory tract, such as reversible airways obstruction and asthma and those used in the treatment and/or prophylaxis of disorders associated with pulmonary hypertension and of disorders associated with right heart failure by inhaled delivery.

One problem associated with inhalers is coordinating the release of the liquid spray with inhalation by the user. It is a further aspect of the present invention that there is provided a means which facilitates this problem.

Accordingly, there is also provided an inhaler, comprising an electrohydrodynamic comminution means, a means for partially or fully discharging the liquid comminution and a conduit through which the liquid comminution is administered, wherein the discharging means is arranged to be activated by inhalation of the user.

Suitably, the electrohydrodynamic comminution means comprises a comminution site and a charging means, the charging means acting directly or by induction to produce the required charge on the comminution means, favourably acting by induction.

Suitably, the electrohydrodynamic comminution means comprises a means for supplying liquid to the comminution means.

One favoured arrangement wherein the discharging means is activated by inhalation of the user comprises a valve means located so as to open and close the conduit, suitably within the conduit, the valve means being opened by inhalation of the user which then activates the discharging means.

A suitable discharging means is provided by one or more capacitors or by a sharp edged or pointed electrode.

When the discharging means is a sharp edged or pointed electrode, the discharging means is preferably operationally attached to the valve means such that when the valve means opens the sharp edged or pointed electrode is thereby exposed to the communited liquid.

A suitable valve means is a flap valve.

In a particular instance the sharp edged or pointed electrode is fixed so as to extend upward from the plane of the flap valve, the flap valve being pivotally fixed so as to open and close the conduit, such that when the flap valve pivots open the sharp edged or pointed electrode pivots into the flight path of the comminuted liquid.

Thus in a most particular instance the invention provides an inhaler, the inhaler comprising an electrohydrodynamic comminution site, a means for supplying liquid to the comminution site, a means for charging the comminution site, a sharp edged or pointed electrode for partially or fully discharging the liquid comminution and a conduit through which the liquid comminution is administered, the conduit having a valve means activated by inhalation of the user, wherein the valve means comprises a flap shaped to seal the conduit, the flap being pivotally fixed so as to open and close the conduit, the sharp edged or pointed electrode extends upwards from the plane of the flap valve, such that in use the flap valve pivots open and the discharging means pivots into the flight path of the comminuted liquid.

When the devices comprise a sharp edged or pointed electrode, the arrangement suitably provides that the sharp edged or pointed electrode is electrically shielded from the liquid comminution when the valve means is closed. One particular method of achieving this is that the sharp edged or pointed electrode pivots into a recess formed in the charging means when the valve means closes.

When used herein 'a comminution' includes a liquid droplet spray.

When used herein 'medicament' includes proprietary medicines, pharmaceutical medicines and veterinary medicines.

When used herein, unless more specifically defined herein, 'inhaled administration' includes administration to and via the upper respiratory tract, including the nasal mucosa, and the lower respiratory tract.

The description 'sharp edged or pointed' when used herein in relation to operational parts of the device, such as the electrode, also includes electrical equivalents thereof and hence includes shapes such as ridges and the like. The essential requirement is that the operational part of the device has, or a component or feature of the device has, dimensions which will give rise to a sufficiently high electrical field strength so as to exceed the breakdown strength of the air. This topic is theoretically described in "Depositional Control of Macroscopic Particles by High Strength Electric Field Propulsion" R A Coffee, in "Transactions of the Institution of Electrical and Electronic Engineers, Industry Applications, U.S.A.", Vol. IA-10 pp 511 to 519, Jul./Aug. 1974. An example is an electrical field strength of approximately 3 million volts per meter.

The liquid medicinal formulations for use in the device of the invention may be formulated according to conventional procedures, such as those disclosed in the U.S. Pharmacopoeia, the European Pharmacopoeia, 2nd Edition, Martindale The Extra Pharmacopoeia, 29th Edition, Pharmaceutical Press and the Veterinary Pharmacopoeia.

The liquid cosmetic formulations for use in the device of the invention may be formulated according to conventional procedures, such as those disclosed in Harry's Cosmeticology, 9th Edition, 1982, George Goodwin, London.

BRIEF DESCRIPTION OF THE DRAWINGS

The invention may now be described, by way of illustration, with reference to the accompanying drawings, in which.

DETAILED DESCRIPTION OF EMBODIMENTS

Figure 1:
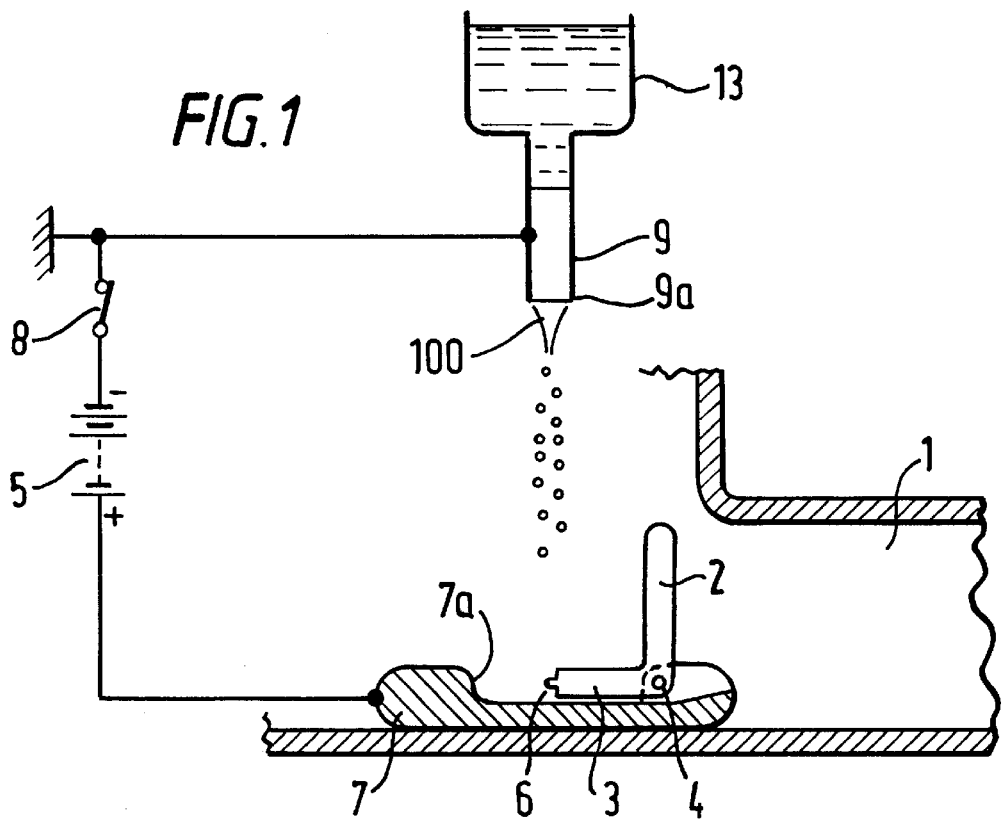
FIGS. 1 and 2 illustrate a device with a hinged flap which effects droplet ionization.
Figure 2:
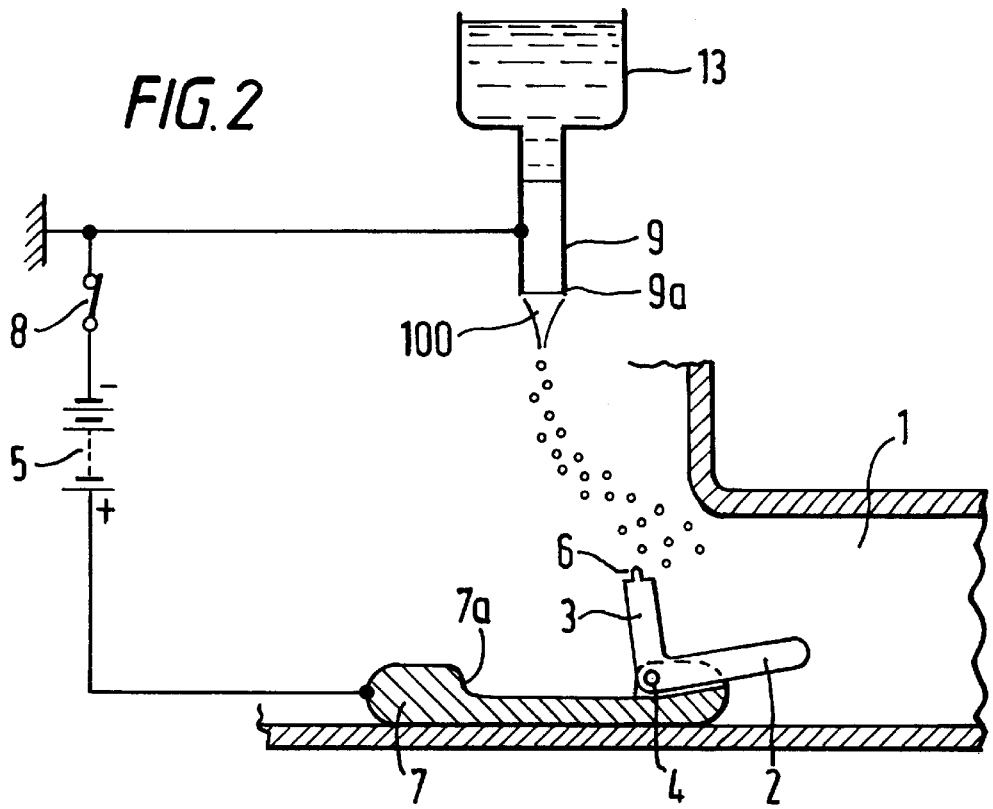

In FIGS. 1 and 2, a device of the invention is illustrated in which a pressure reduction created by the action of breathing through a suitable ducting (1) causes a lightweight flip (2), balanced by a second member (3) pivoted at a hinge (4) and connected to a dc high voltage supply of either polarity (5) to revolve through a sufficient degree of arc to allow the second member of the flap to become exposed to the electric field and then create gaseous ions.

The flap valve thus has two actions: (a) it opens an air passage (1) to facilitate a flow of droplets; and (b) it simultaneously rotates a balancing member (3) attached to the flap (2) through a sufficient degree of arc to expose a ridge, or nipple (6) having one dimension of less than about 1.0 mm radius of curvature.

The ridge, or nipple (6) may be made of any conducting, or semi-conducting material such as metal, or carbon-loaded plastic, and is connected to a source of high voltage (5). When not actuated by breathing, the ridge will be electrically screened in a recess 7a of the surface of a flat electrode (7), also connected to the high voltage source (5). In this position the electrode (7) may be switched on, or off by a simple switch (8).

When switched on, the electrode induces a potential of opposing polarity at the tip (9a) of a nearby nozzle (9). This induced potential causes liquid at the tip of the nozzle to emerge as a fast jet (100) which breaks up into charged droplets. The nozzle (9) is connected to earth.

The invention therefor performs more than one function: (a) the flap valve (2) allows droplets to be inhaled only when the valve is actuated by the act of breathing; (b) the principle of induction, rather than direct, nozzle charging improves the control of droplet size and maximum flow rate, for those liquids which are difficult to atomize by the electrohydrodynamic process; (c) it overcomes the inevitable consequence of induction charging, which is that the opposite polarity droplets would otherwise be so strongly attracted to the source of the induced voltage (7) that the droplets would not be available for delivery by inhalation, or other forms of deposition onto target surfaces.

Figure 3:
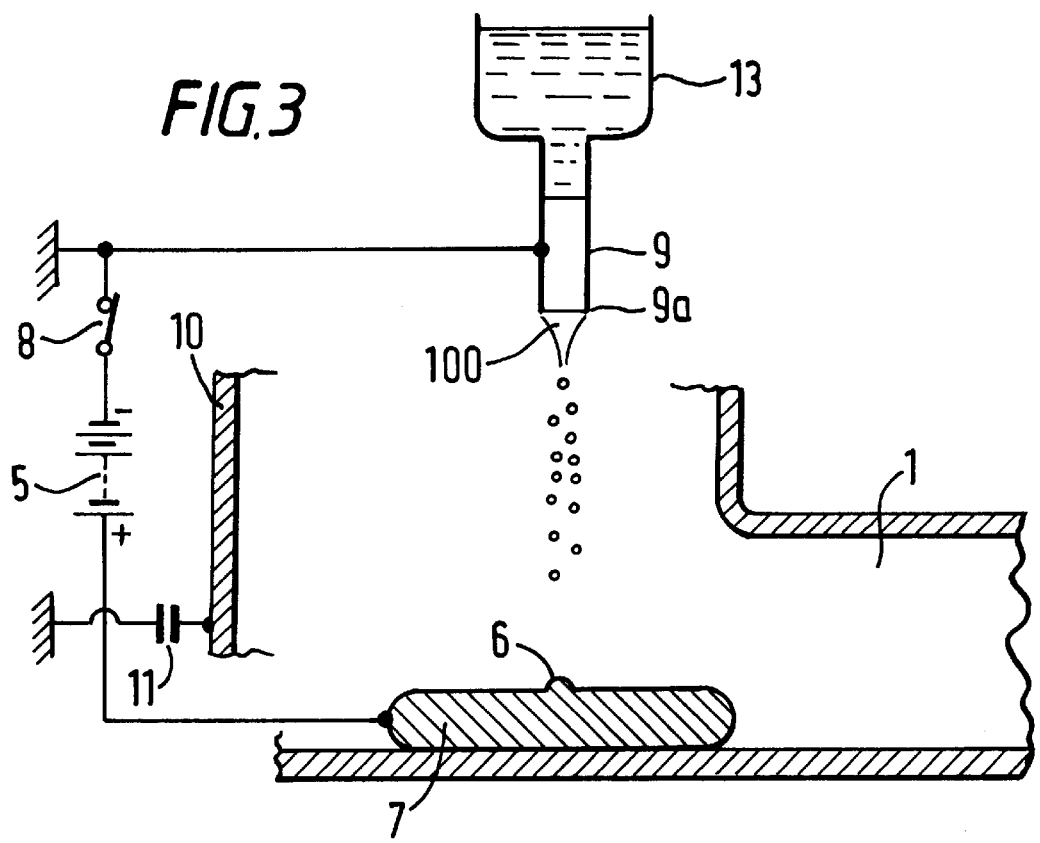
FIG. 3 shows a side view of a device which uses electrically floating conducting surfaces to effect droplet charge.

In FIG. 3, one or more electrically floating conducting or semi-conducting surfaces (10), attached to one or more capacitors (11) are used to attract and capture the gaseous ions so that the electric field created by the electrode (7) acts directly upon the nozzle (8) without impingement of gas ions. Such gas ions, if allowed to reach the nozzle unimpeded would be expected to modify the electric field surrounding the nozzle so as to prevent the emerging liquid from forming the necessary jet (100) of liquid for atomization by the electrohydrodynamic method. The capacitor(s) is chosen to have a time constant of the same order as the time required to established a spray cloud. This time constant will have a value, in seconds, which is the product of the capacitance, C and the resistance, R, of the capacitor. The value of CxR is thus chosen so that the capacitor will charge by bombardment of gaseous ions, until it reaches a sufficient potential to modify the electric field and to re-direct the ions toward the established spray cloud. Generally, the time-constant required will be of the order of seconds or a number of milliseconds. For example, a capacitor of 0.1 microfarad with a resistance of 10 megohms will produce a time constant of one second. FIG. 3 shows one configuration that will create the required induction potential at the nozzle when the electrode (7) is energized and, after a suitable period, dependent upon the position and time constant of the capacitor(s) will then re-arrange the field to allow gaseous ions to migrate into the spray cloud so as to modify the charges on all droplets to a lower (optimal) or approximately zero value. Such droplets may then be readily inhaled.

The charged droplets are prevented from impinging upon the high voltage electrode (7) by the action of fast moving gaseous ions. These ions are created by the combination of electrode voltage, say one to ten kilovolts dc, and the radius of curvature of the small dimension of the ridge or nipple (6) on the balancing member (3) and by juxtaposition of the nozzle (9), the electrode (7) and the capacitor(s) (11). The capacitor(s) (11) may be used to increase the degree of control of the shape of the field and the timing of the essential reshaping process.

Liquid is supplied to the nozzle (9) from either a container (13) by gravity feed, or by mechanical pumping, or by an electrokinetic pumping device. The liquid is supplied to the nozzle and the induced voltage applied by the electrode (7) before the electric field is modified to create gaseous ions by the actuation of the flap-valve (2) and/or the capacitor(s) (11). Then, at any time after the spray cloud is developed, the breath-actuated valve and/or the capacitor(s) is actuated, whereupon the droplet trajectories are modified; moving away from their direct flight to the electrode (7), through the required angle, say to flow by viscous drag in the air movement caused by normal breathing. This action is virtually instantaneous due to the extremely low inertial forces on droplets used for inhalation therapy, which are generally less than about 10.0 $\mu$m in diameter for drug inhalation.

Figure 4:
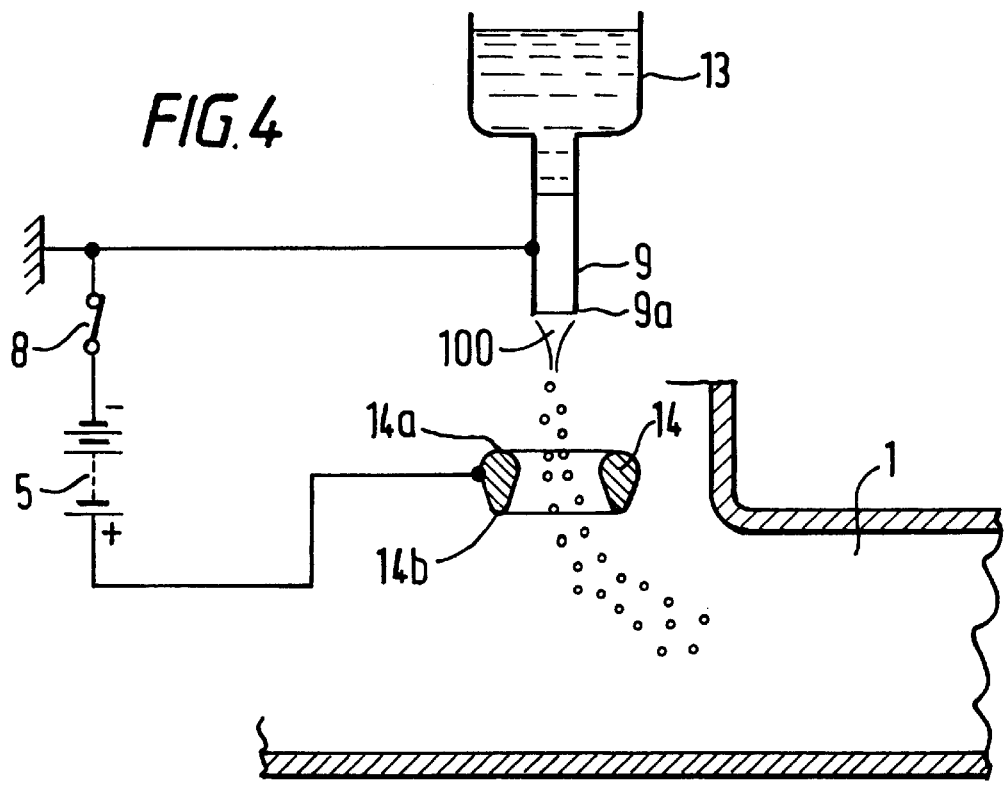
FIG. 4 shows a side view of a device with an induction ring.
Figure 4A:
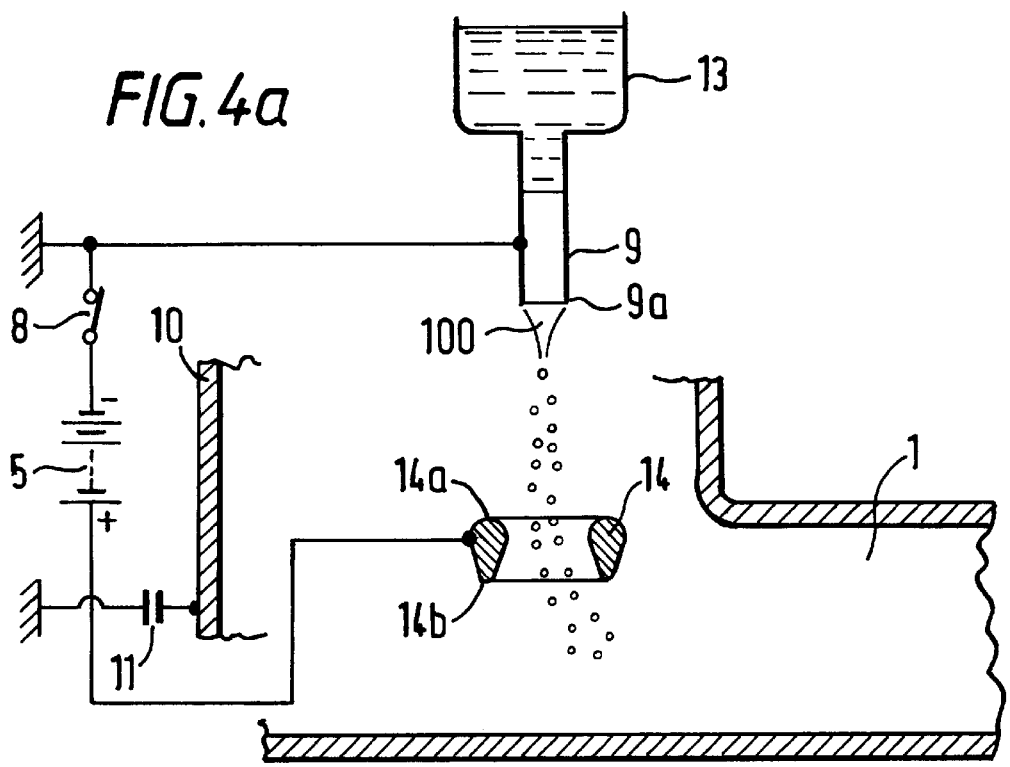
FIGS. 4a and 4b show modifications of the device shown in FIG. 4.
Figure 4B:
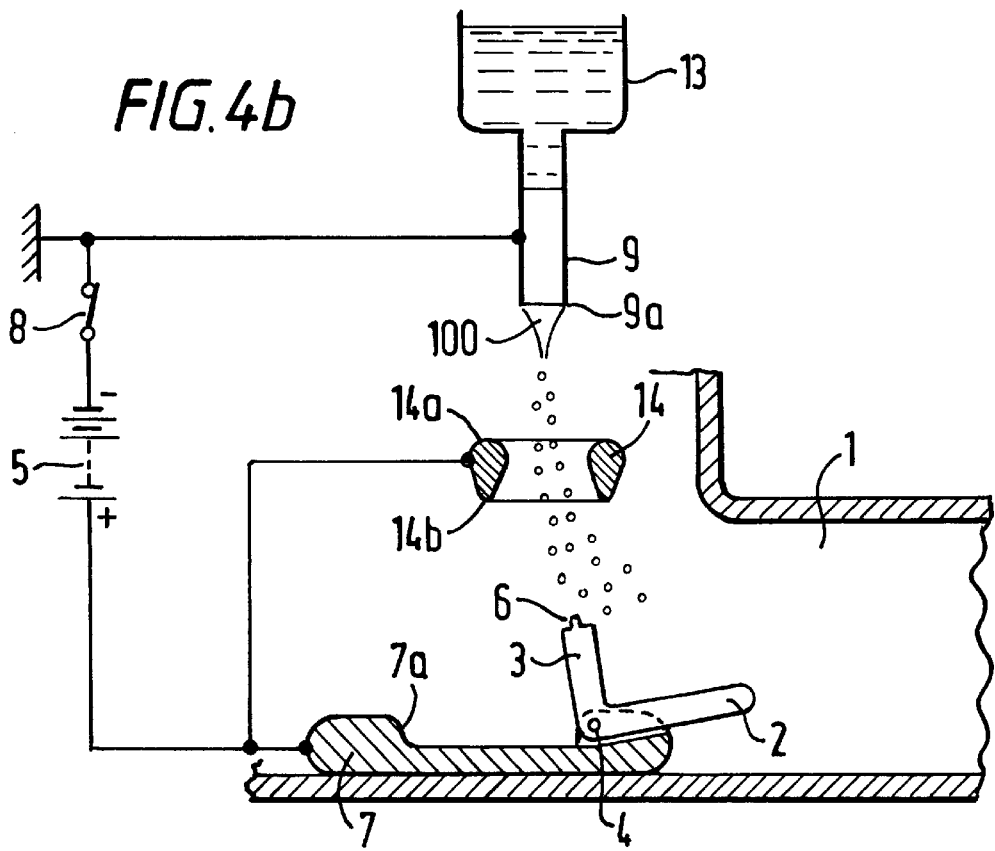

An alternative method of creating the required induction potential to atomize the liquid and subsequently discharge the droplets before impingement upon the induction electrode is to use an induction electrode (14) such as, for example, a ring with two distinct cross-sectional radii of curvature, as shown in FIG. 4. This method may be used with or without a flap valve (2), or field modifying capacitor (s) (11) as shown in FIGS. 4a and 4b. The larger radius (14a) faces towards the nozzle tip, whilst the smaller radius (14b) (say less than about 1.0 mm) faces away from the nozzle (9). It has been found that, by very careful design of the field pattern, charged droplets may have sufficient inertial force to pass through a gap in the electrode (14) without immediate impingement. Although these droplets are then almost immediately forced back to impinge upon the electrode, they may be prevented from doing so by the neutralizing action of the fast moving gaseous ions. It has been further discovered that production of gaseous ions by gas breakdown at the smaller radius of curvature may be delayed by maintaining the field strength at the electrode below the critical value until the charged droplets enter the field, whereupon they will increase the field strength to the critical value and immediately trigger the droplet discharge process.

The critical field strength and shape is a function of: electrode position, shape, and voltage; the relative positions and potentials of the nozzle and capacitor(s) surfaces and the degree and position of space charge potential created by the charged droplets.

It has also been found that the methods of controlled field modification (with time) disclosed herein may be so set as to both discharge and, if required, to recharge the droplets to an optimal value. This could be of importance in, say, ensuring accurate deposition of droplets within a human lung, where both the droplet's mass, and its charge have controlling influence upon the zones of deposition within the system of airways through which the droplets pass during inhalation.

Figure 5:
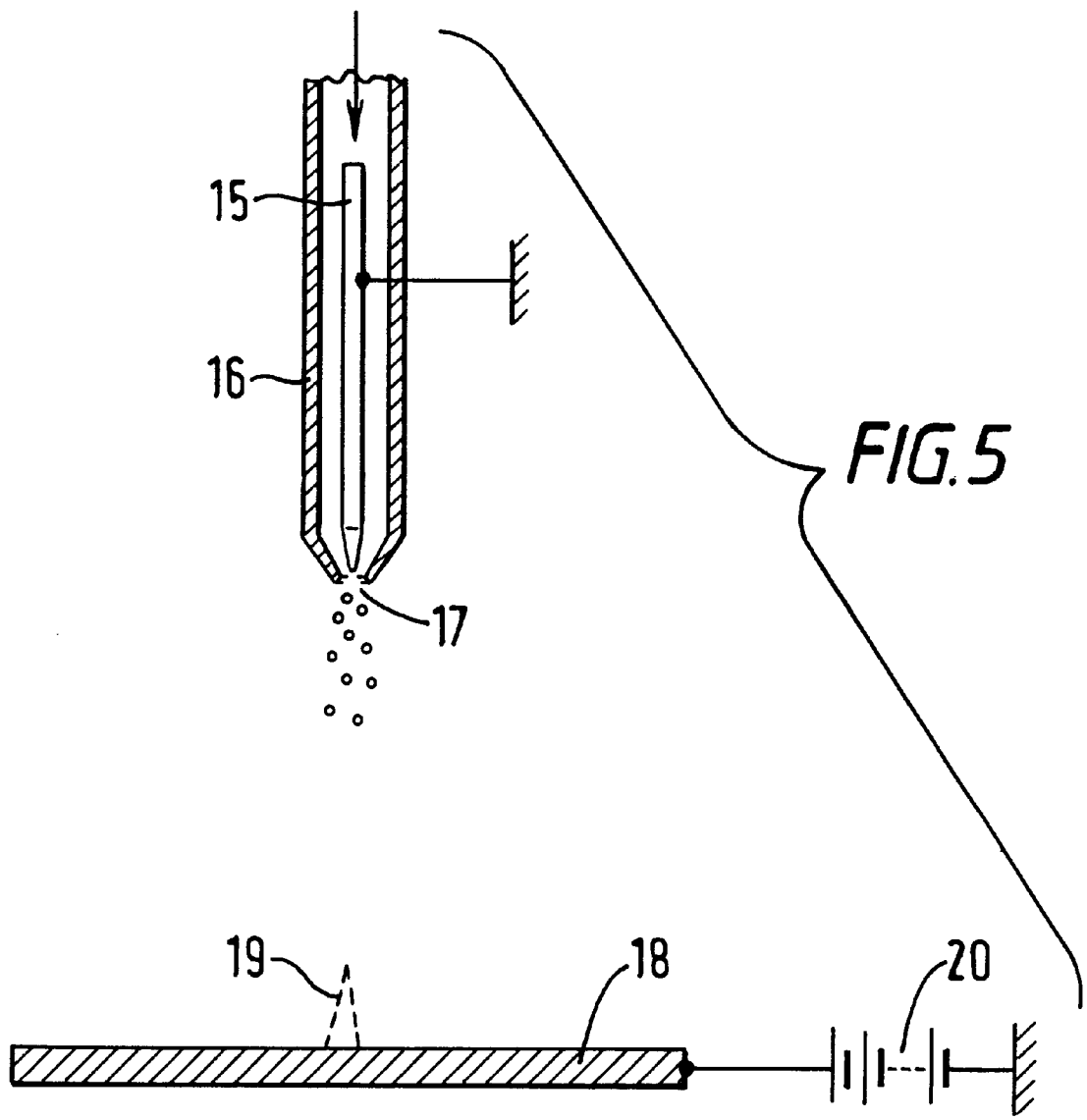
FIG. 5 illustrates a device which uses a controlled field modification technique to both discharge, and recharge droplets to an optimal value.

A particular example of the device and its operation is shown in FIG. 5: An earthed needle, (15) concentrically located within a non-conducting sleeve (16) allowed liquid to flow (by gravity or other light pressure) to an outlet nozzle (17) where the liquid was exposed to a strong convergent electric field provided by a high potential (20) supplied to the flat, smooth surface of electrode (18). This resulted in an induced electrohydrodynamic (EHD) communition of the liquid emerging from capillary nozzle (17).

After the communition was established ( and within less than one second) a sharp element (19) of the induction electrode (18) was exposed.

The exposure of (19) above the smooth surface of (18) produced gaseous ions of the polarity of the high voltage dc. generator (20). Since the EHD spray cloud was induced from an earthed electrode-nozzle (17), the gaseous ions and the spray droplets have opposing polarities. And as the gaseous ions have much greater mobility in the electric field containing both droplets and ions, the droplets were bombarded and hence electrically discharged.

In the experiment described, the distance between tip of nozzle (17) and flat electrode was 30 mm. When the sharp electrode (19) was positioned to discharge the droplets, the distance between tip of nozzle (17) and needle-tip (19) was 23 mm. The liquid flow-rate was 1.34 $\mu$l/sec. The high voltage source was set at a negative potential of 10.7 kilovolts.

The liquid used was 80% ethanol and 20% polyethylene glycol (200), having a viscosity of 2.2 c Poise, a surface tension of 25.0 m N/m, a resistivity of $1.7\times10^3$ ohm.m and a density of 0.86 kg/liter.

The discharging effect was assessed to be essentially 100 per cent.

I claim:

1. A dispensing device comprising an electrohydrodynamic comminution site, a supplier adapted to supply liquid to the comminution site and an induction charger adapted to charge the comminution site to an electrical potential to cause comminution of the liquid, wherein the induction charger is spaced from the comminution site and is arranged to charge the comminution site to the electrical potential that comminutes the liquid by inducing electrical charge at the comminution site.

2. A device according to claim 1, wherein the induction charger comprises a high voltage or piezoelectric generator.

3. A device according to claim 2, wherein the electrical discharger comprises an electrical discharge electrode located downstream of the comminution site.

4. A device according to claim 3, comprising a device adapted to maintain the electrical discharge electrode at ground potential or at a polarity opposite to that to which the induction charger is arranged to charge the comminution site.

5. A device according claim 1, wherein the induction charger and the electrical discharger are provided by an electrode having a first surface which provides the induction charger and is adapted to produce, in response to an electrical potential applied to the electrode, an electrical field adapted to induce the electrical potential to cause comminution of liquid at the comminution site and to cause comminuted matter to substantially by-pass the first surface, and a second surface which provides the electrical discharger and is adapted to produce, in response to the electrical potential, an ionic electric discharge to fully or partially discharge the comminuted matter.

6. A device according to claim 5, wherein the electrode is annular and is located coaxially with respect to the path of comminuted matter from the comminution site, said first surface of the electrode being closer to the comminution site than said second surface, said second surface of the electrode being remote from the comminution site.

7. A device according to claim 2, wherein the electrical discharger comprises an electrical discharge electrode and at least one capacitor adapted to absorb charges from gaseous ions generated by the electrical discharge electrode when an electrical discharge potential is applied to the electrical discharge electrode until a comminution has been established by the comminution site, and adapted to cease to absorb gaseous ions after establishment of the comminution to allow partial or full discharge of the comminution by the gaseous ions.

8. An inhaler comprising a device according to claim 2, wherein said electrical discharger is operable to partially or fully discharge comminuted matter in response to inhalation by a user, further comprising a conduit adapted to supply fully or partially electrically discharged comminuted matter to the user.

9. An inhaler according to claim 8, further comprising a valve adapted to close the conduit, the valve being arranged to be opened by inhalation by a user and so as to activate said electrical discharger upon opening.

10. An inhaler according to claim 9, wherein said electrical discharger comprises a discharge electrode coupled to said valve such that as said valve is opened in response to inhalation by a user, the discharge electrode is exposed to partially or fully electrically discharge comminuted matter formed by the comminution site.

11. An inhaler according to claim 10, wherein the valve is a flap valve and the discharge electrode projects from the plane of the flap valve, the flap valve being pivotally mounted so as to be movable between closed and open positions in response to inhalation by a user such that, as the flap valve pivots to the open position, the discharge electrode is pivoted into the path of the comminuted matter.

12. An inhaler according to claim 10, wherein the discharge electrode is arranged so as to move into a recess formed in said charger when said valve moves to its closed condition.

13. An inhaler comprising a device in accordance with claim 10, for dispensing comminuted matter for inhalation.

14. An inhaler according to claim 8, adapted to dispense comminuted matter for delivery to the upper respiratory tract.

15. An inhaler according to claim 14, adapted to deliver droplets having a diameter from about 10 to about 25 micrometers to the upper respiratory tract.

16. A device according to claim 1, adapted to dispense perfumes, aromas or to enable inhaled delivery of a medicament.

17. A method of dispensing comminuted matter which comprises:

supplying liquid to a comminution site and charging the comminution site to an electrical potential so as to cause comminution of the liquid, wherein the comminution site is charged by induction using a charger spaced from the comminution site.

18. A method according to claim 17, comprising the steps of supplying the liquid to be comminuted and inducing the electrical potential at the comminution site so as to provide droplets for delivery to the upper respiratory tract.

19. A method according to claim 17, which comprises supplying the liquid to be comminuted and inducing the electrical potential at the comminution site so as to provide droplets having a diameter in the range of from about 10 to about 25 micrometers for delivery to the upper respiratory tract.

20. An inhaler comprising a comminution site, a supplier adapted to supply liquid to the comminution site, a charger adapted to charge the comminution site to an electrical potential that causes comminution of the liquid, a discharger adapted to partially or fully electrically discharge the comminuted matter the discharger but not the charger being operable in response to inhalation by a user whereby, in use, after an electrically charged spray cloud has been developed by the charger, inhalation by a user activates the discharger to enable electrical discharging of the charged spray cloud, and a conduit adapted to supply fully or partially electrically discharged comminuted matter to the user.

21. An inhaler according to claim 20, further comprising a valve arranged to close the conduit, the valve being arranged to open in response to inhalation by a user and so as to activate said electrical discharger upon opening.

22. An inhaler according to claim 21, wherein said electrical discharger comprises a discharge electrode coupled to said valve such that, as said valve is opened in response to inhalation by a user, the discharge electrode is exposed to partially or fully electrically discharge comminuted matter formed by the comminution site.

23. An inhaler according to claim 22, wherein the valve is a flap valve and the discharge electrode projects from the plane of the flap valve, the flap valve being pivotally mounted so as to be movable between closed and open positions in response to inhalation by a user such that, as the flap valve pivots to the open position, the discharge electrode is pivoted into the path of the comminuted matter.

24. An inhaler according to claim 22, wherein the discharge electrode is arranged so as to move into a recess formed in said charger as said valve moves to its closed position.

25. An inhaler according to claim 20, adapted to dispense comminuted matter for delivery to the upper respiratory tract.

26. An inhaler according to claim 25, adapted to deliver droplets having a diameter from about 10 to about 25 micrometers to the upper respiratory tract.

* * * * *

UNITED STATES PATENT AND TRADEMARK OFFICE
CERTIFICATE OF CORRECTION

PATENT NO. : 6,105,571
DATED : August 22, 2000
INVENTOR(S) : Ronald Alan Coffee

It is certified that error appears in the above-identified patent and that said Letters Patent is hereby corrected as shown below:

Amend the claims as follows:

Replace Claim 1, at column 8, lines 34-42 to read instead as follows:
1. A dispensing device comprising: an electrohydrodynamic comminution site; a supplier adapted to supply liquid to the comminuton site; an induction charger adapted to charge the comminution site to an electrical potential to cause comminution of the liquid, wherein the induction charger is spaced from the comminution site and is arranged to charger the comminution site to the electrical pontential that comminutes the liquid by inducing electrical charge at the comminution site; and an electrical discharger adapted to partially or fully eletrically discharge comminuted matter before impact on the induction charger.

Claim 3, column 8,
Line 48, change "claim 2" to -- claim 1 --.

Claim 7, column 9,
Line 4, change "claim 2" to -- claim 1 --.

Claim 8, column 9,
Line 1, change "claim 2" to -- claim 1 --.

Replace Claim 17, at Column 9, line 52 to Column 10, line 3 to read instead as follows:

17. A method of dispensing comminuted matter which comprises: supplying liquid to a comminution site and charging the comminution site to an eletrical potential so as to cause comminution of the liquid, wherein the comminution site is charged by induction using a charger spaced from the comminution site; and causing the comminuted matter

UNITED STATES PATENT AND TRADEMARK OFFICE
CERTIFICATE OF CORRECTION

PATENT NO. : 6,105,571
DATED : August 22, 2000
INVENTOR(S) : Ronald Alan Coffee

It is certified that error appears in the above-identified patent and that said Letters Patent is hereby corrected as shown below:

to be partially or fully electrically discharged by an electrical discharger before impact on the induction charger.

Signed and Sealed this

Thirtieth Day of October, 2001

Attest:

*Nicholas P. Godici*

NICHOLAS P. GODICI
*Acting Director of the United States Patent and Trademark Office*

*Attesting Officer*

UNITED STATES PATENT AND TRADEMARK OFFICE
CERTIFICATE OF CORRECTION

PATENT NO. : 6,105,571
DATED : August 22, 2000
INVENTOR(S) : Ronald Alan Coffee

It is certified that error appears in the above-identified patent and that said Letters Patent is hereby corrected as shown below:

Amend the claims as follows:

Column 8, claim 1,
Replace lines 34-42 to read as follows:
1. A dispensing device comprising: an electrohydrodynamic comminution, site; a supplier adapted to supply liquid to the comminution site; and induction charger adapted to charge the comminution site to an electrical potential to cause comminution of the liquid, wherein the induction charger is spaced from the comminution site and is arranged to charge the comminution site to the electrical pontential that comminutes the liquid by inducing electrical charge at the comminution site; and an electrical discharger adapted to partially or fully eltrically discharge comminuted matter before impact on the induction charger.

Column 8, claim 3,
Line 48, change "claim 2" to -- claim 1 --.

Column 9, claim 7,
Line 4, change "claim 2" to -- claim 1 --.

Column 9, claim 8,
Line 1, change "claim 2" to -- claim 1 --.

UNITED STATES PATENT AND TRADEMARK OFFICE
CERTIFICATE OF CORRECTION

PATENT NO.    : 6,105,571
DATED         : August 22, 2000
INVENTOR(S)   : Ronald Alan Coffee It is certified that error appears in the above-identified patent and that said Letters Patent is hereby corrected as shown below:

<u>Column 9,</u>
Replace claim 17, line 52 to column 10, line 3 to read as follows:

17. A method of dispensing comminuted matter which comprises: supplying liquid to a comminution site and charging the comminution site to an electrical potential so as to cause comminution ot the liquid, wherein the comminution site; and is charged by induction using a charger spaced from the comminution site; and causing the comminuted matter to be partially or fully electrically discharged by an electrical discharger before impact on the induction charger.

This certificate supersedes Certificate of Correction issued October 13, 2001

Signed and Sealed this

Fifth Day of March, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.    : 6,105,571
DATED         : August 22, 2000
INVENTOR(S)   : Ronald Alan Coffee It is certified that error appears in the above-identified patent and that said Letters Patent is hereby corrected as shown below:

Column 8,
Replace lines 34-42 to read as follows:
1. A dispensing device comprising: an electrohydrodynamic comminution, site; a supplier adapted to supply liquid to the comminution site; and induction charger adapted to charge the comminution site to an electrical potential to cause comminution of the liquid, wherein the induction charger is spaced from the comminution site and is arranged to charge the comminution site to the electrical potential that comminutes the liquid by inducing electrical charge at the comminution site; and an electrical discharger adapted to partially or fully eletrically discharge comminuted matter before impact on the induction charger.
Line 48, change "claim 2" to -- claim 1 --.

Column 9,
Line 1, change "claim 2" to -- claim 1 --.
Line 4, change "claim 2" to -- claim 1 --.
Line 52, to column 10, line 3, replace claim 17, to read as follows:

17. A method of dispensing comminuted matter which comprises: supplying liquid to a comminution site and charging the comminution site to an electrical potential     so as to cause comminution ot the liquid, wherein the comminution site; and is charged by induction using a charger spaced from the comminution site; and causing the comminuted matter to be partially or fully electrically discharged by an electrical discharger before impact on the induction charger.

This certificate supersedes Certificate of Correction issued March 5, 2002

Signed and Sealed this

Second Day of July, 2002

*Attest:*

JAMES E. ROGAN
*Director of the United States Patent and Trademark Office*

*Attesting Officer*

UNITED STATES PATENT AND TRADEMARK OFFICE
CERTIFICATE OF CORRECTION

PATENT NO.    : 6,105,571                                             Page 1 of 1
DATED         : August 22, 2000
INVENTOR(S)   : Ronald Alan Coffee It is certified that error appears in the above-identified patent and that said Letters Patent is hereby corrected as shown below:

Column 8,
Replace lines 34-42 to read as follows:
 1. A dispensing device comprising: an electrohydrodynamic comminution, site; a supplier adapted to supply liquid to the comminution site; and induction charger adapted to charge the comminution site to an electrical potential to cause comminution of the liquid, wherein the induction charger is spaced from the comminution site and is arranged to charge the comminution site to the electrical potential that comminutes the liquid by inducing electrical charge at the comminution site; and an electrical discharger adapted to partially or fully eltrically discharge comminuted matter before impact on the induction charger.
Line 48, change "claim 2" to -- claim 1 --.

Column 9,
Line 1, change "claim 2" to -- claim 1 --.
Line 4, change "claim 2" to -- claim 1 --.
Line 52, to column 10, line 3, replace claim 17, to read as follows:

17. A method of dispensing comminuted matter which comprises: supplying liquid to a comminution site and charging the comminution site to an electrical potential so as to cause comminution of the liquid, wherein the comminution site is charged by induction using a charger spaced from the comminution site; and causing the comminuted matter to partially or fully electrically discharged by an electrical discharger before impact on the induction charger.

This certificate supersedes Certificate of Correction issued July 2, 2002.

Signed and Sealed this

Twelfth Day of November, 2002

Attest:

Attesting Officer

JAMES E. ROGAN
Director of the United States Patent and Trademark Office